United States Patent [19]

Beaver

[11] Patent Number: 5,292,450
[45] Date of Patent: Mar. 8, 1994

[54] PRODUCTION OF HEXABROMOCYCLODODECANE

[75] Inventor: Phillip R. Beaver, Baton Rouge, La.

[73] Assignee: Ethyl Corporation, Richmond, Va.

[21] Appl. No.: 991,143

[22] Filed: Dec. 16, 1992

Related U.S. Application Data

[63] Continuation of Ser. No. 487,780, Mar. 5, 1990, abandoned.

[51] Int. Cl.$^5$ .......................... C07C 17/02; C09K 3/00
[52] U.S. Cl. ............................ 252/182.12; 252/183.13; 570/246
[58] Field of Search ...................... 252/183.13, 182.12; 570/246

[56] References Cited

U.S. PATENT DOCUMENTS

| | | | |
|---|---|---|---|
| 3,544,641 | 12/1970 | Versuel | 570/246 |
| 3,558,727 | 1/1971 | Jenkner et al. | 260/648 |
| 3,652,688 | 3/1972 | Olechowski et al. | 260/648 |
| 3,833,675 | 9/1974 | Newcombe et al. | 260/648 |
| 4,783,563 | 11/1988 | Taniuchi et al. | 570/246 |
| 4,918,253 | 4/1990 | Hermolin et al. | 570/246 |
| 4,933,412 | 6/1990 | Ito et al. | 524/466 |
| 5,004,848 | 4/1991 | Beaver | 520/206 |
| 5,025,110 | 6/1991 | Beaver | 520/206 |

FOREIGN PATENT DOCUMENTS 2205830 12/1988 United Kingdom ................ 570/246

*Primary Examiner*—Edward A. Miller
*Attorney, Agent, or Firm*—David E. LaRose

[57] ABSTRACT

Improved method by control of excess bromine in reaction between bromine and cyclododecatriene to form hexabromocyclododecane provides increased product yield. A novel reaction mass is obtained and maintained.

6 Claims, No Drawings

PRODUCTION OF HEXABROMOCYCLODODECANE

This application is a continuation of application Ser. No. 487,780, filed Mar. 5, 1990, and now abandoned.

BACKGROUND

Known methods of brominating cyclododecatriene to produce hexabromocyclododecane include admixing bromine and cyclododecatriene for reaction in proportions other than the stoichiometric three moles of bromine to one mole of cyclododecatriene, e.g. an excess of bromine. For examples, see U.S. Pat. No. 3,558,727 (Jenkner et al) and U.S. Pat. No. 3,833,675 (Newcombe et al), incorporated herein by reference in their entirety. However, there remains a need for improved methods to achieve higher purity and yields of the solid hexabromocyclododecane product obtained from the reaction mass formed in the bromination of cyclododecatriene.

SUMMARY

Improved methods have been discovered for brominating cyclododecatriene to produce hexabromocyclododecane of increased purity and yields. These methods comprise critical control by employing an excess of bromine above the stoichiometric amount required for the bromination of cyclododecatriene. A reaction mass is produced from which increased yields are obtained.

DESCRIPTION OF PREFERRED EMBODIMENTS

Embodiments of the present invention comprise steps of the controlled admixing of an amount of cyclododecatriene and an amount of bromine in a solvent reaction media to form and maintain a reaction mass that is substantially free of sub-brominated cyclododecatriene (brominated cyclododecatriene having less than six bromine atoms substituted thereto, e.g. tetrabromocyclododecene). The amount of bromine employed in the reaction is also sufficient for competing reactions which form by-product brominated species. The amount of brominated species formed can preferably be reduced by effective control of the bromine fed to the reaction system.

The solvent reaction medium provides the environment for the bromination of the cyclododecatriene to a hexabromocyclododecane product. The cyclododecatriene reactant can be one of, or a mixture of, the several isomeric forms of cyclododecatriene, e.g. trans,trans,-cis-1,5,9-cyclododecatriene. The bromine used in the bromination can conveniently be supplied by a brominating agent, such as elemental bromine.

The stoichiometric requirement of bromine for the bromination of cyclododecatriene is ideally in the proportions of 3 moles of bromine ($Br_2$) for each mole of cyclododecatriene converted to hexabromocyclododecane. If an insufficient amount of bromine is in the reaction environment to completely brominate the cyclododecatriene to the hexabromine compound, then sub-brominated species of cyclododecatriene can be present. The presence of unreacted cyclododecatriene and sub-brominated cyclododecatriene is a contamination in the recovered hexabromocyclododecane product effecting quality (e.g. reduced melting point characteristics) and requiring additional costs, i.e. additional purification procedures are necessary to reduce the presence of these contaminants and to recover them for recycle or process for disposal.

The solvent reaction medium used with the present invention can conveniently be any reaction media for the bromination of cyclododecatriene, but preferably is a mixed solvent composition comprising an alcohol and a halogenated hydrocarbon. Examples of solvent systems usable can be found in U.S. Pat. Nos. 3,558,727; 3,652,688 and 3,833,675. Preferred solvent compositions are $C_1$–$C_4$ alcohols and $C_1$–$C_4$ halogenated hydrocarbons in which bromine, chlorine or both bromine and chlorine are the halogens. More preferably, the solvents include t-butyl alcohol, ethanol, n-propanol, isopropanol, n-butanol, methanol, butanol-2, 2-methyl propanol-1, carbon tetrachloride, chloroform, isobutyl bromide and dibromomethane. A more preferable solvent system is composed of isobutyl alcohol and chloroform. Another more preferable solvent system is isobutyl alcohol and isobutyl bromide. The weight ratio of halogenated hydrocarbon to alcohol in the solvent system can range from about 1/99 to about 95/5, preferably less (in terms of halogenated hydrocarbon) than about 50/50, more preferably less than about 15/85 (i.e. from about 1/99 to about 15/85).

Bromination of cyclododecatriene in accordance with the present invention comprises admixing an amount of cyclododecatriene and an amount of bromine in a solvent reaction medium to form and maintain a reaction mass that is substantially free of sub-brominated cyclododecatriene, said amount of bromine being sufficient for the unavoidable production of hydrogen bromide and brominated solvent species. Cyclododecatriene reaction with bromine is relatively fast compared to competing reactions. However, the bromine provided will tend to react with hydrogen atoms (such as from cyclododecatriene) in the mixture to form hydrogen bromide. This reaction, the formation of hydrogen bromide, can be competitive with the cyclododecatriene bromination and represents a loss of available bromine for the bromination of cyclododecatriene. Brominating cyclododecatriene in accordance with the present invention must provide sufficient bromine to ensure that substantially complete bromination (i.e. addition of six bromine atoms) of at least substantially all available cyclododecatriene is accomplished.

Therefore, the admixing of bromine and cyclododecatriene in a solvent reaction medium results in several different reactions with differing relative reaction rates. Among the reactions occurring are:

(1) the desired additions of bromine molecule ($Br_2$) to each of the three double bonds of cyclododecatriene (CDT) to produce hexbromocyclododecane (HBCD);

(2) the undesired substitution of —Br at —C—H bonds on CDT or a brominated adduct of CDT, resulting in overbromination of HBCD (i.e. more than the addition of six bromine atoms) and production of hydrogen bromide (HBr); and (3) the undesired side reaction between bromine and the reaction medium, producing hydrocarbons, alkyl bromides and/or hydrogen bromides. For example, isobutanol reaction medium and bromine can react to produce isobutyl isobutyrate, isobutyl bromide and hydrogen bromide.

Reaction (1), the addition of bromine to form HBCD, is relatively faster than reactions (2) and (3) under the reaction conditions employed to form HBCD. Nonetheless, reactions (2) and (3) occur sufficiently to the extent to produce about four-tenths (0.4) moles of hydrogen bromide (HBr) per mole of cyclododecatriene (CDT) fed to the reaction mass. Reactions (2) and (3) result in a decrease of available bromine for reaction with cyclododecatriene to form hexabromocyclododecane.

Heretofore, an excess of bromine was provided relative to the stoichiometric quantities of bromine to form hexabromocyclododecane alone without recognition of the surprising criticality of maintaining specific excesses of bromine on a continuous as well as an overall basis relative to the other reactions occurring. Criticality exists in maintaining an excess of bromine within limits so as not to have too low or too high an excess, thereby obtaining higher than heretofore expected yields and selectivity in the hexabromocyclododecane products produced.

For example, when bromine and cyclododecatriene are reacted to produce hexabromocyclododecane, intermediate products dibromocyclododecadiene and tetrabromocyclododecene are produced. Whereas the hexabromocyclododecane (HBCD) produced has much lower solubility in the solvent solutions typically used and, accordingly, a substantial portion of the HBCD precipitates from the solutions, dibromocyclododecadiene and tetrabromocyclododecene remain in solution and are available for the heretofore discussed undesired substitution reactions. When the concentration of these intermediates in solution increase, such as when an insufficient amount of bromine is available, then the undesired reactions increase. Some of the intermediates, especially tetrabromocyclododecene, can become incorporated into the precipitating HBCD, resulting in both a contamination of the HBCD and a reduction in the yield of HBCD due to incomplete bromination of these intermediates. Importantly, and unrecognized heretofore, an over excess of bromine results in an increase of undesirable substitution reactions with cyclododecatriene (CDT), CDT adducts and reaction medium, resulting again in product contamination during coprecipitation and reduced yield from loss of intermediates to form HBCD. Thus, the bromine feed ratio in accordance with the present invention must be controlled on a continuous basis and not merely provided to the system as an initial addition of excess bromine.

The following reactions (not stoichiometrically balanced) are further illustrative of the bromination of cyclododecatriene (CDT) in a solvent comprising alcohol to produce hexabromocyclododecane:

$$2Br_2 + CDT \rightarrow \text{tetrabromocyclododecene (tetra)} \quad (I)$$

$$Br_2 + \text{tetra} \rightarrow \text{hexabromocyclododecane (HBCD)} \quad (II)$$

$$Br_2 + \text{tetra} \rightarrow \text{substituted species} + HBr \quad (III)$$

$$Br_2 + CDT \rightarrow \text{substituted species} + HBr \quad (IV)$$

$$Br_2 + ROH \rightarrow RBr + HBr \quad (V)$$

$$Br_2 + ROH \rightarrow RR + HBr \quad (VI)$$

Equation (II) represents the desired reaction to produce the hexabromocyclododecane (HBCD) product. Equation (I) represents the failure to achieve full bromination of cyclododecatriene. Tetrabromocyclododecene is a contaminant to the HBCD product, lowering the melting point of the HBCD product. Typical strategies to reduce or eliminate this contaminant involve providing an excess of bromine beyond the stoichiometric amount for reaction with cyclododecatriene. However, tetrabromocyclododecene will precipitate with hexabromocyclododecane in solution, resulting in tetrabromocyclododecene being trapped within the HBCD particles and being reduced in availability for further bromination. Equation (III) represents a deleterious effect of the presence of tetrabromocyclododecene.

Known prior strategies to provide an excess of bromine did not recognize, appreciate nor compensate for the reactions (III), (IV), (V) and (VI). Reactions (I) and (II) are relatively fast compared to reactions (III) through (VI). Prior art methods of providing an excess of bromine can be performed in an attempt to complete bromination of tetrabromocyclododecene to HBCD, but providing an uncontrolled excess of bromine drives the reactions of Reactions (III), (IV), (V) and (VI), further contaminating the HBCD product and unnecessarily resulting in bromine loss and in increased downstream purification and recovery costs. Embodiments of the present invention reduce the heretofore unknown or unappreciated detrimental results from such excess bromine by use of appropriate control of excess bromine.

In accordance with the present invention a reaction mass composition comprises the following:
 (i) a solvent medium in which bromine, cyclododecatriene, hydrogen bromide and brominated species of the components of the solvent media are substantially soluble;
 (ii) hexabromocyclododecane;
 (iii) from 0% to about 6% by weight sub-brominated and non-brominated cyclododecatriene relative to the hexabromocyclododecane;
 (iv) from about 0.3% to about 10% by weight hydrogen bromide relative to the hexabromocyclododecane;
 (v) from about 0% to about 10% by weight brominated solvent species relative to said hexabromocyclododecane; and
 (vi) free bromine.

Free bromine is uncombined, elemental bromine. This composition can afford high-yield recovery with enhanced purity upon being processed by standard separation techniques for the recovery of a hexabromocyclododecane product from a reaction mass.

Embodiments in accordance with the present invention ensure that practically at no time is there present in the reaction medium cyclododecatriene an unnecessary excess of the bromine available for the bromination of cyclododecatriene, thereby avoiding unnecessary amounts of brominated by-products.

Another process for the manufacture of a hexabromocyclododecatriene product in accordance with the invention comprises the steps of
 (a) forming a reaction mass which initially contains
  (i) an initial amount of bromine,
  (ii) an initial amount of cyclododecatriene, and
  (iii) an initial amoutn of a solvent reaction media in which bromine and cyclododecatriene are substantially soluble, and
 (b) maintaining said reaction mass under reaction conditions while adding an additional amount of bromine and an additional amount of cyclododecatriene to form a hexabromocyclododecane product from said initial and additional amounts of bromine and cyclododecatriene,
wherein effective control of said initial and additional amounts of bromine and cyclododecatriene in said steps of forming and maintaining is performed such that said reaction mass is substantially free of sub-brominated and non-brominated cyclododecatriene to effectively increase the yield of said hexabromocyclododecane product. Compensation for the formation of hydrogen bromide can be deemed to be implicit.

Operations in accordance with embodiments of the present invention can additionally compensate for operational errors which might be caused by imperfect metering and measuring devices and operations. An embodiment of the present invention can comprise the steps immediately hereinabove plus additionally provide that prior to the introduction of any cyclododecatriene into the solvent reaction media a first amount of bromine is fed or provided, the first amount being sufficient to compensate for operational errors in the introducing of the initial and additional amounts of bromine and cyclododecatriene such that the cyclododecatriene is never in stoichiometric excess relative to the amount of bromine available for reaction with the cyclododecatriene in the solvent reaction media. In a batch reactor, the first amount of bromine preferably usable could range from about 0.05% to about 0.6% by weight of the total amount of bromine added for the stoichiometric bromination, this first amount being in addition to the stoichiometric amount.

As noted herein above, preferred solvents are mixtures of an alcohol and a halogenated hydrocarbon, more preferably chloroform or alkyl bromide, e.g. isobutyl bromide.

Bromination of cyclododecatriene in accordance with the present invention can be performed in either continuous or batch operations. It is preferred in batch reactions that from about 1% to about 10% by weight bromine in excess of the stoichiometric requirement for reaction with cyclododecatriene fed to produce hexabromocyclododecane be present. Preferably, about 6% to about 9% by weight excess bromine should be present for solvent systems relatively high in alcohol proportion (e.g. greater than about 60%).

The following experiments illustrate embodiments of the invention, but are not intended to limit the invention to a particular set of parameters.

EXPERIMENT NO. 1

About 148.1 grams (g) bromine (0.3 weight percent in excess of stoichiometric requirement) were weighted into a volumetrically calibrated charge cylinder with micro flowcock, where micro flowcock refers to a laboratory valve capable of fractional dropwise control of liquid feed. About 50 g cyclododecatriene (CDT), 70 g isobutanol (IBA) and 70 g chloroform were thoroughly mixed and weighed into a separate charge cylinder with micro flowcock. About 20 g IBA and 20 g chloroform were charged into a well stirred reaction flask.

The reaction flask and contents were heated to 45° C. for temperature control. Flow of bromine from its cylinder into the reaction flask was started at a known valve setting to 45 minutes feed time. About 30 seconds later, flow of the CDT in solvents was started at a rate sufficient to have a feed time of 44.5 minutes. Volumes were recorded during the 45 minute feed period and feed ratio was kept constant until both reactants had been fed completely. Temperature was kept at 45° C. for an additional 45 minutes. A test at this time showed that there was no bromine (unreacted) in the system.

The reaction mass was neutralized to a pH range of 7 to 8 with 5.4 g (0.29 mole/mole CDT feed) monoethanol amine. Then the reaction mass was filtered on a Buchner funnel to separate crude, HBCD solids. The HBCD solids were rinsed with about 10 g isobutanol. Next, the cake on the funnel was washed with four 200 g portions of distilled water to remove solid monoethanol amine hydro-bromide and other water soluble bromides. Finally, the wet cake was removed and dried until weight loss rate was negligible. Yield based on CDT was 86%.

EXPERIMENTS 2 THROUGH 6

These experiments were conducted just as in Experiment 1, except that amounts and feed rates for bromine were such that the amount of excess bromine was increased to 2.2, 3.9, 6.2, 8.3 and 10.4 weight percent, respectively. There was no free bromine after the hold period in Experiment 2, but there was free bromine in the system for all other runs.

EXPERIMENT 7

This experiment was like Experiments 1–6, except that excess bromine used was 5 weight percent and neutralizing agent was sodium carbonate solution.

EXPERIMENT 8

This experiment was like Experiments 1–6, except that excess bromine of 4.5% was charged into the pot before simultaneous feeding of stoichiometric bromine and CDT began. Also, all of the solvents used (100.7 g IBA and 99.7 g chloroform) were in the reactor from the start.

Results

Significant results from these runs are tabulated below:

| Exp. No. | % Excess Bromine | Free Br2 | % Yield on CDT | Base Req'd Mole/mole | Melt Point, °C. Initial | Melt Point, °C. Final |
|---|---|---|---|---|---|---|
| 1 | 0.3 | No | 86.0 | 29 | 174 | 188 |
| 2 | 2.2 | No | 89.8 | 30 | 176 | 188 |
| 3 | 3.9 | Yes | 96.2 | 30 | 176 | 186 |
| 4 | 6.2 | Yes | 89.3 | 44 | 174 | 188 |
| 5 | 8.3 | Yes | 87.2 | 56 | 176 | 187 |
| 6 | 10.4 | Yes | 87.1 | 60 | na | na |
| 7 | 5.0 | Yes | 95.4 | 21 | 179 | 187 |
| 8 | 4.5 | Yes | 89.6 | 36 | 179 | 184 |

What is claimed is:

1. A method for brominating cyclododecatriene with bromine in a batch operation, said process comprising:
   (a) charging a reaction vessel, containing a solvent reaction media in which bromine and cyclododecatriene are substantially soluble, with a first amount of bromine, said first amount being an amount in the range from about 0.05 to about 0.6 weight percent of the stoichiometric amount of bromine needed to form hexabromocyclododecane from cyclododecatriene, based on the total amount of cyclododecatriene being brominated;
   (b) subsequent to the charging in step (a), concomitantly adding to the reaction vessel cyclododecatriene and a second amount of bromine, the respective rates of addition of said cyclododecatriene and second amount of bromine being such that, at all times during this addition, the second amount of bromine being added is within the range of from about 1 to about 10 weight percent in excess of the stoichiometric amount of bromine required to form hexabromocyclododecane from said cyclododecatriene, based on the amount of cyclododecatriene being charged to the reaction vessel.

2. The method of claim 1 wherein said solvent comprises an alcohol and a halogenated hydrocarbon.

3. The method of claim 2 where said halogenated hydrocarbon is chloroform.

4. The method of claim 2 wherein said halogenated hydrocarbon is isobutyl bromide.

5. The method of claim 2 wherein the alcohol is isobutanol.

6. The method of claim 1 wherein the second amount of bromine is within the range of from about 6 to about 9 weight percent in excess of the stoichiometric amount of bromine required to form hexabromocyclododecane from said cyclododecatriene, based on the amount of cyclododecatriene being charged to the reaction vessel.

* * * * *